US012577578B2

(12) United States Patent
Wang et al.

(10) Patent No.: US 12,577,578 B2
(45) Date of Patent: Mar. 17, 2026

(54) APPLICATION OF RICE NAT PROTEIN AND CODING GENE THEREOF IN REGULATION AND CONTROL OF PLANT DISEASE RESISTANCE

(71) Applicant: Sichuan Agricultural University, Chengdu (CN)

(72) Inventors: Jing Wang, Chengdu (CN); Xuewei Chen, Chengdu (CN); Xiang Lu, Chengdu (CN); Qing Xiong, Chengdu (CN); Qian Yan, Chengdu (CN)

(73) Assignee: Sichuan Agricultural University, Chengdu (CN)

( * ) Notice: Subject to any disclaimer, the term of this patent is extended or adjusted under 35 U.S.C. 154(b) by 0 days.

(21) Appl. No.: 19/212,531

(22) Filed: May 19, 2025

(65) Prior Publication Data

US 2025/0313851 A1     Oct. 9, 2025

Related U.S. Application Data

(63) Continuation of application No. PCT/CN2025/075678, filed on Feb. 5, 2025.

(30) Foreign Application Priority Data

Apr. 8, 2024     (CN) .......................... 202410415333.4

(51) Int. Cl.
*C12N 15/82*          (2006.01)
(52) U.S. Cl.
CPC ................................ *C12N 15/8282* (2013.01)
(58) Field of Classification Search
None
See application file for complete search history.

(56) References Cited

U.S. PATENT DOCUMENTS 9,096,865 B2 *   8/2015   Vinocur ............. C12N 15/8271

FOREIGN PATENT DOCUMENTS

| | | |
|---|---|---|
| CN | 104805062 A | 7/2015 |
| CN | 107151675 A | 9/2017 |
| CN | 113061171 A | 7/2021 |
| CN | 115747251 A | 3/2023 |
| CN | 116479034 A | 7/2023 |
| WO | 2021160079 A1 | 8/2021 |

OTHER PUBLICATIONS

Retrieval report-First search dated Jul. 31, 2024 in SIPO application No. 202410415333.4.
Notice of first Office action dated Aug. 6, 2024 in SIPO application No. 202410415333.4.
Notice of Second Office action dated Sep. 9, 2024 in SIPO application No. 202410415333.4.
Retrieval report-Supplementary search dated Sep. 26, 2024 in SIPO application No. 202410415333.4.
Notification to Grant Patent Right for Invention dated Jan. 13, 2025 in SIPO application No. 202410415333.4.
International Search Report issued in corresponding PCT Application No. PCT/CN2025/075678 dated Mar. 11, 2025.
Unknown Definition, "[RNA cytidine acetyltransferase 1, *Oryza sativa Japonica* Group]" NCBI Reference Sequence: XP_015620417.1 , Aug. 7, 2018 , Origin Genbank claims involved : 1-7.
Zhu, Ziwei, et al., Magnaporthe oryzae effector MoSPAB1 directly activates rice Bsr-d1 expression to facilitate pathogenesis, Nature Communications, Dec. 18, 2023, p. 1-12, Chapter 8399, vol. 14:8399 doi: 10.1038/s41467-023-44197-9 claims involved : 1-7.
Mao Yan, et al., Recent progress on rice resistance to blast disease, Scientia Sinica Vitae, Sep. 24, 2021, pp. 1495-1510, vol. 52, Issue 10 doi: 10.1360/SSV-2021-0012 claims involved : 1-7.

* cited by examiner

*Primary Examiner* — Medina A Ibrahim
(74) *Attorney, Agent, or Firm* — Piloff Passino & Cosenza LLP; Rachel K. Piloff; Sean A. Passino

(57)          ABSTRACT

An application of rice NAT protein and a coding gene thereof in regulation and control of plant disease resistance, a method for regulating and controlling rice resistance to rice blast and a method for cultivating transgenic rice with high resistance to rice blast are provided. In the research of rice immune response, a gene NAT of which the translation is induced by *M. oryzae* is identified and obtained.

2 Claims, 11 Drawing Sheets

Specification includes a Sequence Listing.

Target 1 : In 1bp (frameshift)

KO1
WT

35S          NAT

WT    KO1 KO2

*NAT*

```
                            SEQUENCE LISTING

Sequence total quantity: 11
SEQ ID NO: 1              moltype = DNA  length = 3075
FEATURE                  Location/Qualifiers
source                   1..3075
                         mol_type = other DNA
                         organism = synthetic construct
SEQUENCE: 1
atgaggaaga aggtggacga gcgcatccgg acgctgatcg agaacggcgt gcgggagcgg   60
cagcggtcca tgttcgtcat cgtcggcgac aagtcgcgcg accagatcgt caacctcaac  120
tacatgctcg ccaagtcccg cgtcaagtcc cgcccctccg tcctctggtg ctaccgcgac  180
aagctcgaga tcagcagcca caagaagaag cgggccaagc agatcaagaa gctcatgcag  240
aggggctca tggaccccga gaaggccgac cccttctcgc tcttcttgga gacgtctgac   300
atcacctact gcctctacaa ggactccgag agggttcttg gcaacacatt cggcatgtgc  360
atcctgcagg attttgaggc gctcacgccc aacctactcg cgaggaccat cgagacggtt  420
gagggtggtg gtttgatcat cctgctgctc cgctcccttt cctctctcac cagtctttat  480
acaatggtca tggatgtcca tgaaagattc cggacagagt cgcatacccca ggctgctgct  540
aggttcaacg agaggttctt gctatccata gcgtcttgca aatcatgtgt cgtcatggat  600
gacgaactca acattttgcc tatatcctct cacatgaaat ttatacaacc agttacgaac  660
aatgaggatt ctgagggact gtcagaaagg gagagagagt tgaaagatct aaaagatcaa  720
ttccgtgaag acttccagt tggtccttta attggaaagt gcttcacgat ggatcagggt  780
aaagctgtga tcaatttcct tgactctatt ttggacaagt ccctgaggag cacagttgcc  840
ttgcttgctg ctcgcggacg cgggaaatca gctgcccttg gtcttgctat tgctggagcc  900
attgctgctg ggtattcaaa catatttgtc acagccccaa gtccagagaa cctaaaaaca  960
ctgtttgatt ttgtgtgcaa gggaatgaat gcactggagt acaaggagca tttgcattat 1020
gatgtggtga agagtgcaga tccagaactc aagaaggcaa ctattcaaat aaatgtctac 1080
aagcagcatc gtcagacgat ccagtatctg aaaccacatg atcatgggaa gctttctcaa 1140
gttgagctcc ttgtcattga tgaagctgct gctattccat tgccaattgt taagtccttg 1200
cttggtccat accttgtttt cctatcatcc actgtcaatg ggtacgaagg aactgggcga 1260
tccttgtctt tgaagctcct acagcagttg gaatcccaaa gccagccatc tgctccaaat 1320
aatggaccca attcaagtag gctttttaag aaaattgaat taaatgagtc cattaggtat 1380
gcatctggtg atcctattga gagctggctt aatgatttac tttgtttgga tcttgcgaac 1440
tccatcccca atatcagtag gctacctcat ccaaaagaat gtgatcttta ttatgtcaac 1500
cgagacacac ttttctcata tcataaggag agtgagatat ttttacagcg gatgatggca 1560
ctttatgttg cttcccatta caaaaattca cccaatgact tgcaactaat ggctgatgcg 1620
ccggctcatc acctatttgt attgcttggc ccagtcgatg agtctaaaaa tcagctcccg 1680
gatattctat gtgtagtcca ggtctgtttg gaaggtcaaa tatctcgaaa atcagctatg 1740
aaaagcctaa gtgagggtcg gtcaccttct ggtgatcaaa taccatggaa attttgtgaa 1800
cagtttcaag acaacgtgtt tccaagtctc tcaggagctc ggattgtacg aattgctgtc 1860
catccaagtg ctgtgaggct tggatatggt tcagctgctg tggaccttt gacaaggtac 1920
tatgaagggc aaatgactct atttgctgag gatgaggagg aaaatgaaga gcctgaagtc 1980
aggatcactg aggctgcaga gaaggcttct ctactagaag agaccgtaaa gcctagggca 2040
aatctcccac cactccttgt ccatcttcgc gaacgtcgtc ctgaaaagct ccattatctt 2100
ggtgtatctt ttggacttac acaagagctt ttccgttttt ggcggaagca caacttctat 2160
ccattctatg tgggccaaat tcctagtgct gtgactggtg agcatacttg tatggtcttg 2220
aggccttaa atagcgatga cattgaagtt aatgagtcaa gcaaatgtgg atttttggat 2280
ccattttatc aagatttcag acaaagattc aggcgtctct taggaacatc tttccggcat 2340
ctcaattta agcttgcaat gagtgtattg gcttccaaga ttgatttttc agatcacgaa 2400
ccctcagact attataccaa tattacctca aagatattgg gagatatgct atcaccacat 2460
gatatgaagc ggctggaagc atattctaac aatttggtcg attatcatct gattctggac 2520
cttgtcccta ttcttgcaca ccagtatttt tcagagaagc ttcctgttac actacatggt 2580
gcccaagcag ctgttttgtt ctgtatggga ctacaagaca aagacatagg tgctacaaag 2640
gaagaactgg ggatagagag ggaacaggt ctatcaaact tcatcaagac aatgaagaag 2700
ttatacggtt accttcataa tattgcagga aaagaaattg aagcaacatt accacgacta 2760
aaggaaattg atacagctcc tcttaaatca ttggatgagg accttgatga agcagccagg 2820
gaagtaaagg aacaaagaag agcaatagat gaggatgatg tggacccaaa gtttctgcaa 2880
aagtatgcaa ttgatgccga tgacgatgag attgagaagg cgctgaacgg aggaaagatt 2940
tccgcaagcg gtgttatcag tgtgaaatcc aacaagacaa aggctgacaa gcaagagaag 3000
```

```
cgcaaagaaa tgaagaaatc aaaaaggaaa ggaaatgatg gagagaaatc tgagtctaag   3060
aagaagaggt cttga                                                     3075

SEQ ID NO: 2             moltype = AA   length = 1024
FEATURE                  Location/Qualifiers
source                   1..1024
                         mol_type = protein
                         organism = synthetic construct
SEQUENCE: 2
MRKKVDERIR TLIENGVRER QRSMFVIVGD KSRDQIVNLN YMLAKSRVKS RPSVLWCYRD    60
KLEISSHKKK RAKQIKKLMQ RGLMDPEKAD PFSLFLETSD ITYCLYKDSE RVLGNTFGMC    120
ILQDFEALTP NLLARTIETV EGGGLIILLL RSLSSLTSLY TMVMDVHERF RTESHTQAAA    180
RFNERFLLSI ASCKSCVVMD DELNILPISS HMKFIQPVTN NEDSEGLSER ERELKDLKDQ    240
FREDFPVGPL IGKCFTMDQG KAVINFLDSI LDKSLRSTVA LLAARGRGKS AALGLAIAGA    300
IAAGYSNIFV TAPSPENLKT LFDFVCKGMN ALEYKEHLHY DVVKSADPEL KKATIQINVY    360
KQHRQTIQYL KPHDHGKLSQ VELLVIDEAA AIPLPIVKSL LGPYLVFLSS TVNGYEGTGR    420
SLSLKLLQQL ESQSQPSAPN NGPNSSRLFK KIELNESIRY ASGDPIESWL NDLLCLDLAN    480
SIPNISRLPH PKECDLYYVN RDTLFSYHKE SEIFLQRMMA LYVASHYKNS PNDLQLMADA    540
PAHHLFVLLG PVDESKNQLP DILCVVQVCL EGQISRKSAM KSLSEGRSPS GDQIPWKFCE    600
QFQDNVFPSL SGARIVRIAV HPSAVRLGYG SAAVDLLTRY YEGQMTLFAE DEEENEEPEV    660
RITEAAEKAS LLEETVKPRA NLPPLLVHLR ERRPEKLHYL GVSFGLTQEL FRFWRKHNFY    720
PFYVGQIPSA VTGEHTCMVL RPLNSDDIEV NESSKCGFLD PFYQDFRQRF RRLLGTSFRH    780
LNFKLAMSVL ASKIDFSDHE PSDYYTNITS KILGDMLSPH DMKRLEAYSN NLVDYHLILD    840
LVPILAHQYF SEKLPVTLHG AQAAVLFCMG LQDKDIGATK EELGIEREQV LSNFIKTMKK    900
LYGYLHNIAG KEIEATLPRL KEIDTAPLKS LDEDLDEAAR EVKEQRRAID EDDVDPKFLQ    960
KYAIDADDDE IEKALNGGKI SASGVISVKS NKTKADKQEK RKEMKKSKRK GNDGEKSESK    1020
KKRS                                                                 1024

SEQ ID NO: 3             moltype = DNA   length = 20
FEATURE                  Location/Qualifiers
source                   1..20
                         mol_type = other DNA
                         organism = synthetic construct
SEQUENCE: 3
cgaacgtcgt cctgaaaagc                                                20

SEQ ID NO: 4             moltype = DNA   length = 20
FEATURE                  Location/Qualifiers
source                   1..20
                         mol_type = other DNA
                         organism = synthetic construct
SEQUENCE: 4
atatgcttcc agccgcttca                                                20

SEQ ID NO: 5             moltype = DNA   length = 20
FEATURE                  Location/Qualifiers
source                   1..20
                         mol_type = other DNA
                         organism = synthetic construct
SEQUENCE: 5
atgaggaaga aggtggacga                                                20

SEQ ID NO: 6             moltype = DNA   length = 23
FEATURE                  Location/Qualifiers
source                   1..23
                         mol_type = other DNA
                         organism = synthetic construct
SEQUENCE: 6
tcaagacctc ttcttcttag act                                            23

SEQ ID NO: 7             moltype = DNA   length = 23
FEATURE                  Location/Qualifiers
source                   1..23
                         mol_type = other DNA
                         organism = synthetic construct
SEQUENCE: 7
aacgtgtttc caagtctctc agg                                            23

SEQ ID NO: 8             moltype = DNA   length = 25
FEATURE                  Location/Qualifiers
source                   1..25
                         mol_type = other DNA
                         organism = synthetic construct
SEQUENCE: 8
tgtgaacgtg tttccaagtc tctcg                                          25

SEQ ID NO: 9             moltype = DNA   length = 25
FEATURE                  Location/Qualifiers
source                   1..25
```

-continued

```
                        mol_type = other DNA
                        organism = synthetic construct
SEQUENCE: 9
aaaacgagag acttggaaac acgtt                                        25

SEQ ID NO: 10          moltype = DNA  length = 41
FEATURE                Location/Qualifiers
source                 1..41
                       mol_type = other DNA
                       organism = synthetic construct
SEQUENCE: 10
ggacagggta cccggggatc catgaggaag aaggtggacg a                      41

SEQ ID NO: 11          moltype = DNA  length = 41
FEATURE                Location/Qualifiers
source                 1..41
                       mol_type = other DNA
                       organism = synthetic construct
SEQUENCE: 11
ggtactagtg tcgactctag aagacctctt cttcttagac t                      41
```

APPLICATION OF RICE NAT PROTEIN AND CODING GENE THEREOF IN REGULATION AND CONTROL OF PLANT DISEASE RESISTANCE

CROSS-REFERENCE TO RELATED APPLICATIONS

This application is a continuation of PCT/CN2025/075678, filed on Feb. 5, 2025 and claims priority of Chinese Patent Application No. 202410415333.4, filed on Apr. 8, 2024, the entire contents of which are incorporated herein by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:

File name: sequence.xml
Creation date: May 14, 2025
Byte size: 15,052

TECHNICAL FIELD

The disclosure relates to the field of biotechnology, in particular to the application of rice N-terminal acetyltransferase (NAT) protein and coding gene thereof in regulation and control of plant disease resistance.

BACKGROUND

Fungal diseases such as rice blast cause large-scale crop yield reduction, so cultivating disease-resistant crops is one of the main goals of planting industry. Many genes related to plant disease resistance have been reported, including effector genes and regulatory genes, which come from crops such as rice, wheat, corn, soybean and model plant *Arabidopsis thaliana*. Some of them have been used as target genes in crop disease-resistant genetic engineering, and successfully cultivated disease-resistant rice, wheat, corn, soybean and so on. However, due to the difference of genetic background, the application of some genes is hindered, so new related genes are still needed to meet the needs of breeding.

As one of the most important food crops, it is of great theoretical and practical significance to improve the disease resistance of rice.

N-terminal acetyltransferases (NATs) play an important role in the process of plant development, so the previous research on NATs focused on the plant development in which NATs participated. However, there is no report about applying NAT gene to plant disease resistance.

SUMMARY

The purpose of the disclosure is to provide the application of rice NAT protein and coding gene thereof in regulation and control of plant disease resistance, so as to solve the problems existing in the prior art. NAT is regulating and controlling rice disease resistance, and the rice disease resistance may be improved by overexpressing NAT in rice.

In order to achieve the above objectives, the present disclosure provides the following scheme.

The disclosure provides an application of NAT protein in any of following:

(1) an application in regulation and control of plant disease resistance;

(2) an application in preparing products for regulating and controlling the plant disease resistance;

(3) an application in cultivating disease-resistant plant varieties; and (4) an application in preparing products for cultivating disease-resistant plant varieties.

The amino acid sequence of the NAT protein is a protein sequence as shown in SEQ ID NO: 2 or including an amino acid sequence as shown in SEQ ID NO: 2. The amino acid sequence of the NAT protein may also be a derivative protein with the same function, which is obtained by substitution and/or deletion and/or addition of one or more amino acid residues in the sequence of SEQ ID NO: 2, or a protein with more than 80% identity with the sequence of SEQ ID NO: 2 and the same function. It may also be a fusion protein obtained by connecting a protein-tag to the N-terminal or/and C-terminal of the protein shown above.

The above identity refers to the identity of amino acid sequence. Homology retrieval sites on the Internet may be used to determine the identity of amino acid sequences, such as the BLAST page of NCBI homepage. For example, in Advanced BLAST2.1, by using blastp as a program, setting the Expect value to 10, setting all Filter to OFF, using BLOSUM62 as a Matrix, setting the Gap existence cost, Per residue gap cost and Lambda ratio to 11, 1 and 0.85 (the default values) respectively, and searching for the identity of a pair of amino acid sequences to calculate, and then getting the identity value (%).

The above 80% or more identity may be at least 81%, 82%, 85%, 86%, 88%, 90%, 91%, 92%, 95%, 96%, 98%, 99% or 100% identity.

The above-mentioned protein-tag refers to a polypeptide or protein that is fused and expressed with the target protein by using DNA recombination technology in vitro, so as to facilitate the expression, detection, tracing and/or purification of the target protein. The protein-tag may be GFP tag, Flag tag, His tag, MBP tag, HA tag, myc tag, GST tag and/or SUMO tag, etc.

The disclosure also provides an application of a coding gene of NAT protein in any of following:

(1) an application in regulation and control of plant disease resistance;

(2) an application in preparing products for regulating and controlling the plant disease resistance;

(3) an application in cultivating disease-resistant plant varieties; and (4) an application in preparing products for cultivating disease-resistant plant varieties.

The amino acid sequence of the NAT protein is a protein sequence as shown in SEQ ID NO: 2 or including an amino acid sequence as shown in SEQ ID NO: 2. The nucleotide sequence of the coding gene is a gene sequence as shown in SEQ ID NO: 1 or including the nucleotide sequence as shown in SEQ ID NO: 1.

The disclosure also provides an application of a recombinant vector including a coding gene of NAT protein in any of following:

(1) an application in regulation and control of plant disease resistance;

(2) an application in preparing products for regulating and controlling the plant disease resistance;

(3) an application in cultivating disease-resistant plant varieties; and (4) an application in preparing products for cultivating disease-resistant plant varieties.

The amino acid sequence of the NAT protein is a protein sequence as shown in SEQ ID NO: 2 or including an amino acid sequence as shown in SEQ ID NO: 2. The nucleotide sequence of the coding gene is a gene sequence as shown in SEQ ID NO: 1 or including the nucleotide sequence as shown in SEQ ID NO: 1.

The disclosure also provides an application of host bacteria including a recombinant vector in any of following:

(1) an application in regulation and control of plant disease resistance;

(2) an application in preparing products for regulating and controlling the plant disease resistance;

(3) an application in cultivating disease-resistant plant varieties; and (4) an application in preparing products for cultivating disease-resistant plant varieties.

The recombinant vector is an expression vector integrating NAT gene. The nucleotide sequence of NAT gene is the gene sequence shown in SEQ ID NO: 1 or including the nucleotide sequence as shown in SEQ ID NO: 1.

Optionally, the way of regulating and controlling plant disease resistance includes:

improving the disease resistance of the plant by overexpressing NAT gene in the plant; or reducing the disease resistance of the plant by knocking out NAT gene in the plant, and improving the susceptibility to diseases.

Optionally, the plant includes a Gramineae plant.

The disclosure also provides a method for regulating and controlling plant disease resistance, including any one of the following methods:

(1) improving the disease resistance of the plant by overexpressing NAT gene in the plant; and (2) reducing the disease resistance of the plant by knocking out NAT gene in the plant, and improving the susceptibility to diseases.

The nucleotide sequence of NAT gene is the gene sequence shown in SEQ ID NO: 1 or including the nucleotide sequence as shown in SEQ ID NO: 1.

Optionally, the plant includes a Gramineae plant.

The disclosure also provides a method for cultivating transgenic plants with high disease resistance, including the following steps: by overexpressing NAT genes in plants, increasing the expression amount of the NAT genes, and obtaining transgenic plants with high disease resistance.

Optionally, the nucleotide sequence of the NAT gene is the gene sequence as shown in SEQ ID NO: 1 or including the nucleotide sequence as shown in SEQ ID NO: 1.

The plants include Gramineae plants.

The disclosure discloses the following technical effects.

In the research of rice immune response, the inventor of the present disclosure identifies a gene induced by *Magnaporthe oryzae* (*M. oryzae*), names it NAT, and analyzes that it belongs to the NAT family. Experiments prove that overexpression of NAT gene and improvement of protein expression have the function of obviously improving the rice disease resistance. It shows that NAT gene is regulating and controlling plant disease resistance, and NAT protein and its coding gene are of great significance for cultivating disease-resistant rice varieties.

BRIEF DESCRIPTION OF THE DRAWINGS

In order to explain the embodiments of the present disclosure or the technical scheme in the prior art more clearly, the drawings needed in the embodiments will be briefly introduced below. Obviously, the drawings described below are only some embodiments of the present disclosure, and other drawings may be obtained according to these drawings without creative work for ordinary people in the field.

DETAILED DESCRIPTION OF THE EMBODIMENTS

Figure 1:
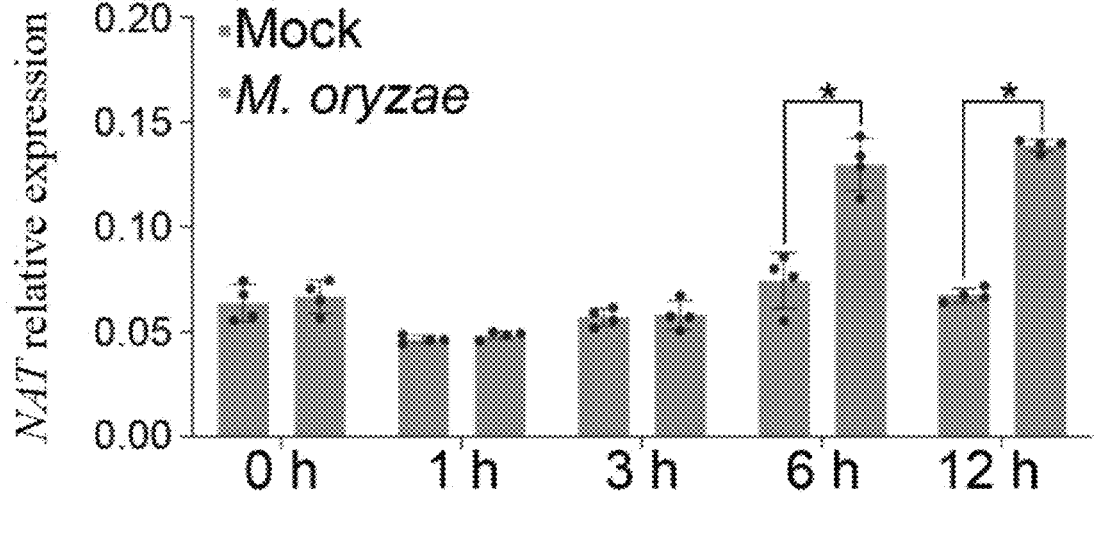
FIG. 1 shows that leaves of three-week-old ZH11 plants are sampled at different time points after being inoculated with *M. oryzae* to detect the relative expression of NAT.

A number of exemplary embodiments of the present disclosure will now be described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges may be independently included or excluded from the range.

Unless otherwise specified, all technical and scientific terms used herein have the same meaning as commonly understood by one of ordinary skill in the art to which this disclosure relates. Although the present disclosure only describes the preferred methods and materials, any methods and materials similar or equivalent to those described herein may also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the disclosure. The description and embodiment of the present disclosure are exemplary only.

The terms "comprising", "including", "having" and "containing" used in this article are all open terms, which means including but not limited to.

Some experimental materials and reagents involved in the following embodiments:

(1) rice variety Zhonghua 11 (O. *Sativa L.* spp. *japonica*, var zhonghua11, AA genome, ZH11) belongs to *japonica* subspecies, which is recorded in the following documents: Ni Yuchong, Rice Flower Culture New Variety-Zhonghua 11, *Agricultural Science and Technology Newsletter*, 1989, 07, 35; provided by Professor Chen Xuewei from Institute of Genetics and Developmental Biology, Chinese Academy of Sciences.

(2) NAT overexpression transgenic rice is completed by Boyuan Biotechnology Company.

(3) Plant binary expression vector pTCRISPR, provided by Associate Professor Tang Yongyan, State Key Laboratory of Sichuan Agricultural University.

Plant binary expression vector pCAMBIA2300, provided by Professor Wu Xianjun from Rice Research Institute of Sichuan Agricultural University.

(4) Total RNA extraction kit: purchased from TRIzol of Invitrogen, USA, with the article number of 15596026.

Reverse transcription kit: purchased from HiScript III RT SuperMix for qPCR (+gDNA wiper) of Vanzyme, China, with the article number of R323-01.

Fluorescence quantitative kit: purchased from AceQ qPCR SYBR Green Master Mix of Vanzyme, China, with the article number of Q111-02.

Homologous recombination kit: purchased from ClonExpress II One Step Cloning Kit of Vanzyme, China, with the article number of C112-01.

Embodiment 1 Induced Gene NAT in Rice Immune Response and Cloning Thereof

In the process of studying the immune response of rice, it is found that the expression of NAT is induced by *M. oryzae*. The expression of NAT at each time point infected by rice blast is verified by polymerase chain reaction. Three-week-old ZH11 is used as the research material, and the leaves of ZH11 plants are inoculated with *M. oryzae*. The specific groups are as follows.

Experimental group (*M. oryzae*): applying solution containing $5 \times 10^5$ per milliliter (·mL-1) spores of *M. oryzae* (physiological race Zhong Oct. 8, 2014) and 0.1% Tween20.

Control group (Mock): spray 0.1% Tween20 solution.

Rice leaves are taken at 0 hour (0 H), 1 hour (1 H), 3 hours (3 H), 6 hours (6 H) and 12 hours (12 H) respectively. After total RNA is extracted by Trizol, it is reverse transcribed into cDNA and the relative expression of NAT is detected. The designed primers are:

```
NAT_qPCRF (SEQ ID NO: 3):
5'-CGAACGTCGTCCTGAAAAGC-3';
and

NAT_qPCRR (SEQ ID NO: 4):
5'-ATATGCTTCCAGCCGCTTCA-3'.
```

Using the Experimental group and Control group cDNA as templates, the expression level of the gene is determined by fluorescence quantitative PCR. The results are shown in FIG. 1. There is no significant difference in the relative expression of NAT at 0 H, 1 H and 3 H, but it is found that the relative expression of NAT in the Experimental group is significantly improved compared with the control treatment at 6 H and 12 H after inoculation.

After sequencing analysis, the gene encodes NAT. According to the reference gene sequence of rice genome, primers are designed:

```
NAT_F (SEQ ID NO: 5):
5'-ATGAGGAAGAAGGTGGACGA-3';
and

NAT_R (SEQ ID NO: 6):
5'-TCAAGACCTCTTCTTCTTAGACT-3'.
```

Figure 2:
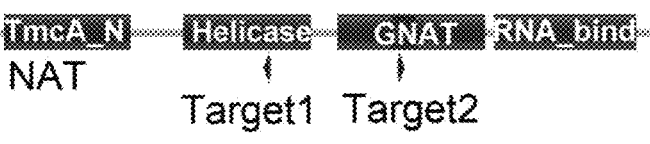
FIG. 2 is a schematic diagram for analyzing the protein domain, conserved acetyl-CoA binding pocket motif and knockout Target of NAT.

Using the total cDNA of ZH11 as a template, about 3.7 kilobase (Kb) DNA bands are amplified by the above primers. It is confirmed to be a NAT gene belonging to NATs family after sequencing. Comparing the LOC_Os12g07300 sequence in the rice genome reference sequence with the cloned sequence obtained from the total cDNA amplification of ZH11, it is shown that the cloned sequence obtained in ZH11 is the same as the LOC_Os12g07300 sequence. The amino acid sequence of NAT protein is shown in SEQ ID NO: 2, and its structural analysis is shown in FIG. 2. CDS sequence of coding chain of gene NAT encoding NAT protein is a DNA molecule shown in SEQ ID NO: 1.

SEQ ID NO: 1 is as follows.

```
ATGAGGAAGAAGGTGGACGAGCGCATCCGGACGCTGATCGAGAAC

GGCGTGCGGGAGCGGCAGCGGTCCATGTTCGTCATCGTCGGCGAC

AAGTCGCGCGACCAGATCGTCAACCTCAACTACATGCTCGCCAAG

TCCCGCGTCAAGTCCCGCCCCTCCGTCCTCTGGTGCTACCGCGAC

AAGCTCGAGATCAGCAGCCACAAGAAGAAGCGGGCCAAGCAGATC

AAGAAGCTCATGCAGAGGGGGCTCATGGACCCCGAGAAGGCCGAC

CCCTTCTCGCTCTTCTTGGAGACGTCTGACATCACCTACTGCCTC

TACAAGGACTCCGAGAGGGTTCTTGGCAACACATTCGGCATGTGC

ATCCTGCAGGATTTTGAGGCGCTCACGCCCAACCTACTCGCGAGG

ACCATCGAGACGGTTGAGGGTGGTGGTTTGATCATCCTGCTGCTC
```

-continued

```
CGCTCCCTTTCCTCTCTCACCAGTCTTTATACAATGGTCATGGAT

GTCCATGAAAGATTCCGGACAGAGTCGCATACCCAGGCTGCTGCT

AGGTTCAACGAGAGGTTCTTGCTATCCATAGCGTCTTGCAAATCA

TGTGTCGTCATGGATGACGAACTCAACATTTTGCCTATATCCTCT

CACATGAAATTTATACAACCAGTTACGAACAATGAGGATTCTGAG

GGACTGTCAGAAAGGGAGAGAGAGTTGAAAGATCTAAAAGATCAA

TTCCGTGAAGACTTTCCAGTTGGTCCTTTAATTGGAAAGTGCTTC

ACGATGGATCAGGGTAAAGCTGTGATCAATTTCCTTGACTCTATT

TTGGACAAGTCCCTGAGGAGCACAGTTGCCTTGCTTGCTGCTCGC

GGACGCGGGAAATCAGCTGCCCTTGGTCTTGCTATTGCTGGAGCC

ATTGCTGCTGGGTATTCAAACATATTTGTCACAGCCCCAAGTCCA

GAGAACCTAAAAACACTGTTTGATTTTGTGTGCAAGGGAATGAAT

GCACTGGAGTACAAGGAGCATTTGCATTATGATGTGGTGAAGAGT

GCAGATCCAGAACTCAAGAAGGCAACTATTCAAATAAATGTCTAC

AAGCAGCATCGTCAGACGATCCAGTATCTGAAACCACATGATCAT

GGGAAGCTTTCTCAAGTTGAGCTCCTTGTCATTGATGAAGCTGCT

GCTATTCCATTGCCAATTGTTAAGTCCTTGCTTGGTCCATACCTT

GTTTTCCTATCATCCACTGTCAATGGGTACGAAGGAACTGGGCGA

TCCTTGTCTTTGAAGCTCCTACAGCAGTTGGAATCCCAAAGCCAG

CCATCTGCTCCAAATAATGGACCCAATTCAAGTAGGCTTTTTAAG

AAAATTGAATTAAATGAGTCCATTAGGTATGCATCTGGTGATCCT

ATTGAGAGCTGGCTTAATGATTTACTTTGTTTGGATCTTGCGAAC

TCCATCCCCAATATCAGTAGGCTACCTCATCCAAAAGAATGTGAT

CTTTATTATGTCAACCGAGACACACTTTTCTCATATCATAAGGAG

AGTGAGATATTTTTACAGCGGATGATGGCACTTTATGTTGCTTCC

CATTACAAAAATTCACCCAATGACTTGCAACTAATGGCTGATGCG

CCGGCTCATCACCTATTTGTATTGCTTGGCCCAGTCGATGAGTCT

AAAAATCAGCTCCCGGATATTCTATGTGTAGTCCAGGTCTGTTTG

GAAGGTCAAATATCTCGAAAATCAGCTATGAAAAGCCTAAGTGAG

GGTCGGTCACCTTCTGGTGATCAAATACCATGGAAATTTTGTGAA

CAGTTTCAAGACAACGTGTTTCCAAGTCTCTCAGGAGCTCGGATT

GTACGAATTGCTGTCCATCCAAGTGCTGTGAGGCTTGGATATGGT

TCAGCTGCTGTGGACCTTTTGACAAGGTACTATGAAGGGCAAATG

ACTCTATTTGCTGAGGATGAGGAGGAAAATGAAGAGCCTGAAGTC

AGGATCACTGAGGCTGCAGAGAAGGCTTCTCTACTAGAAGAGACC

GTAAAGCCTAGGGCAAATCTCCCACCACTCCTTGTCCATCTTCGC

GAACGTCGTCCTGAAAAGCTCCATTATCTTGGTGTATCTTTTGGA

CTTACACAAGAGCTTTTCCGTTTTTGGCGGAAGCACAACTTCTAT

CCATTCTATGTGGGCCAAATTCCTAGTGCTGTGACTGGTGAGCAT

ACTTGTATGGTCTTGAGGCCCTTAAATAGCGATGACATTGAAGTT

AATGAGTCAAGCAAATGTGGATTTTTGGATCCATTTTATCAAGAT
```

-continued

```
TTCAGACAAAGATTCAGGCGTCTCTTAGGAACATCTTTCCGGCAT

CTCAATTTTAAGCTTGCAATGAGTGTATTGGCTTCCAAGATTGAT

TTTTCAGATCACGAACCCTCAGACTATTATACCAATATTACCTCA

AAGATATTGGGAGATATGCTATCACCACATGATATGAAGCGGCTG

GAAGCATATTCTAACAATTTGGTCGATTATCATCTGATTCTGGAC

CTTGTCCCTATTCTTGCACACCAGTATTTTTCAGAGAAGCTTCCT

GTTACACTACATGGTGCCCAAGCAGCTGTTTTGTTCTGTATGGGA

CTACAAGACAAAGACATAGGTGCTACAAAGGAAGAACTGGGGATA

GAGAGGGAACAGGTTCTATCAAACTTCATCAAGACAATGAAGAAG

TTATACGGTTACCTTCATAATATTGCAGGAAAAGAAATTGAAGCA

ACATTACCACGACTAAAGGAAATTGATACAGCTCCTCTTAAATCA

TTGGATGAGGACCTTGATGAAGCAGCCAGGGAAGTAAAGGAACAA

AGAAGAGCAATAGATGAGGATGATGTGGACCCAAAGTTTCTGCAA

AAGTATGCAATTGATGCCGATGACGATGAGATTGAGAAGGCGCTG

AACGGAGGAAAGATTTCCGCAAGCGGTGTTATCAGTGTGAAATCC

AACAAGACAAAGGCTGACAAGCAAGAGAAGCGCAAAGAAATGAAG

AAATCAAAAAGGAAAGGAAATGATGGAGAGAAATCTGAGTCTAAG

AAGAAGAGGTCTTGA.
```

SEQ ID NO: 2 is as follows.

```
MRKKVDERIRTLIENGVRERQRSMFVIVGDKSRDQIVNLNYMLAK

SRVKSRPSVLWCYRDKLEISSHKKKRAKQIKKLMQRGLMDPEKAD

PFSLFLETSDITYCLYKDSERVLGNTFGMCILQDFEALTPNLLAR

TIETVEGGGLIILLLRSLSSLTSLYTMVMDVHERFRTESHTQAAA

RFNERFLLSIASCKSCVVMDDELNILPISSHMKFIQPVTNNEDSE

GLSERERELKDLKDQFREDFPVGPLIGKCFTMDQGKAVINFLDSI

LDKSLRSTVALLAARGRGKSAALGLAIAGAIAAGYSNIFVTAPSP

ENLKTLFDFVCKGMNALEYKEHLHYDVVKSADPELKKATIQINVY

KQHRQTIQYLKPHDHGKLSQVELLVIDEAAAIPLPIVKSLLGPYL

VFLSSTVNGYEGTGRSLSLKLLQQLESQSQPSAPNNGPNSSRLFK

KIELNESIRYASGDPIESWLNDLLCLDLANSIPNISRLPHPKECD

LYYVNRDTLFSYHKESEIFLQRMMALYVASHYKNSPNDLQLMADA

PAHHLFVLLGPVDESKNQLPDILCVVQVCLEGQISRKSAMKSLSE

GRSPSGDQIPWKFCEQFQDNVFPSLSGARIVRIAVHPSAVRLGYG

SAAVDLLTRYYEGQMTLFAEDEEENEEPEVRITEAAEKASLLEET

VKPRANLPPLLVHLRERRPEKLHYLGVSFGLTQELRFWRKHNFY

PFYVGQIPSAVTGEHTCMVLRPLNSDDIEVNESSKCGFLDPFYQD

FRQRFRRLLGTSFRHLNFKLAMSVLASKIDFSDHEPSDYYTNITS

KILGDMLSPHDMKRLEAYSNNLVDYHLILDLVPILAHQYFSEKLP

VTLHGAQAAVLFCMGLQDKDIGATKEELGIEREQVLSNFIKTMKK
```

-continued
LYGYLHNIAGKEIEATLPRLKEIDTAPLKSLDEDLDEAAREVKEQ

RRAIDEDDVDPKFLQKYAIDADDDEIEKALNGGKISASGVISVKS

NKTKADKQEKRKEMKKSKRKGNDGEKSESKKKRS*.

Embodiment 2 Construction of NAT Plant Knockout Vector (1) Construction of NAT Overexpression Vector pTCRISPR-sgRNANAT Taking the genome of rice ZH11 as a template, the designed knockout Target sequence is AACGTGTTTC-CAAGTCTCTCAGG (SEQ ID NO: 7).

And synthesizing the following primer:

```
F (SEQ ID NO: 8):
5'-TGTGAACGTGTTTCCAAGTCTCTCG-3';
and

R (SEQ ID NO: 9):
5'-AAAACGAGAGACTTGGAAACACGTT-3'.
```

After denaturation at 95 degrees Celsius (° C.), it is annealed to form double strands. The pTCRISPR vector is digested by BsaI, and the linearized vector is recovered. The DNA double strands and linearized vectors are mixed according to the system shown in Table 1 below, and T4 DNA ligase ligation reaction is carried out and incubated at room temperature for 30 minutes.

TABLE 1

| Reagent | Dosage |
| --- | --- |
| DNA double-stranded fragment | 0.5-4 microliters (μL) |
| Linearized vector | 0.5-4 μL |
| T4 ligase | 2 μL |
| ddH₂O | X μL |
| Total volume is 10 μL. | |

Figure 3:
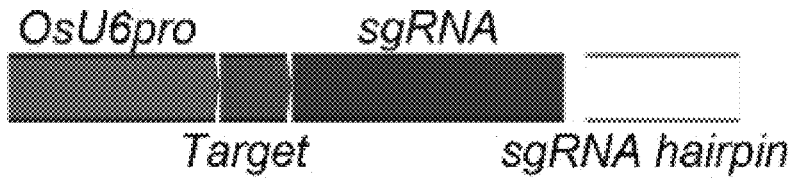
FIG. 3 is a schematic structural diagram of NAT knockout vector.

The pTCRISPR-sgRNA$^{NAT}$ knockout vector is obtained after connection (see FIG. 3).

(2) Transformation

The knockout vector constructed above is transformed into DH5a competent state. After kanamycin screening, monoclonal clones are selected for colony PCR identification. After plasmid extraction and sequencing of positive colonies are correct, it is confirmed that pCAMBIA2300-NAT is correct, and genetic transformation may be carried out.

(3) Construction of Knockout Transgenic Rice

NAT knockout transgenic rice is completed by Boyuan Biotechnology Company.

Figure 4A:
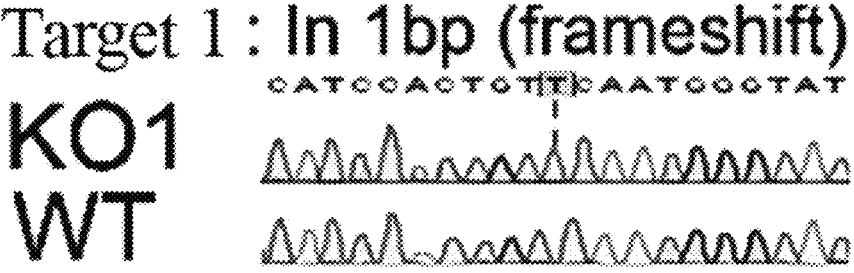
FIG. 4A shows the sequencing results of knockout Target of knockout strain NAT-KO1.
Figure 4B:
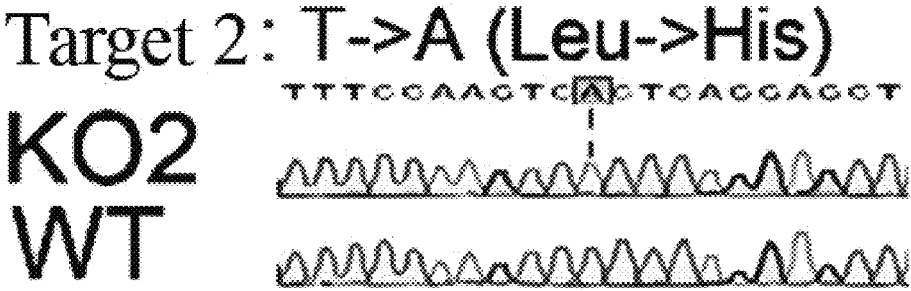
FIG. 4B shows the sequencing results of knockout Target of knockout strain NAT-KO2.

NAT knockout strains NAT-KO1 and NAT-KO2 with ZH11 background and genetic stability are selected and sequenced. Compared with the wild-type strain sequence, it is found that the target sequence of the knockout strain has base insertion or mutation, and the results are shown in FIG. 4A and FIG. 4B.

Embodiment 3 Construction of NAT Plant Expression Vector (1) Construction of NAT Overexpression Vector pCAM-BIA2300-NAT Using the cDNA obtained by reverse transcription of total RNA of rice ZH11 as a template, the cloning primers are as follows.

```
F (SEQ ID NO: 10):
5'-GGACAGGGTACCCGGGGATCCATGAGGAAGAAGGTGGACGA-3';
and

R (SEQ ID NO: 11):
5'-GGTACTAGTGTCGACTCTAGAAGACCTCTTCTTCTTAGACT-3'.
```

The full-length cDNA of NAT is obtained by PCR amplification, and the vector pCAMBIA2300-35S-eGFP-OCS is digested with BamHI and XbaI, and the linearized vector is recovered. According to the system shown in Table 2 below, the full-length cDNA of NAT recovered from the above PCR is mixed with linearized vector for homologous recombination.

TABLE 2

| Reagent | Dosage |
| --- | --- |
| DNA fragment | 0.5-5 μL |
| Linearized vector | 0.5-5 μL |
| 5 × CE II Buffer | 4 μL |
| Exnase II | 2 μL |
| ddH₂O | X μL |
| Total volume is 20 μL. | |

Figure 5:
FIG. 5 is a schematic structural diagram of NAT overexpression vector.

The recombinant vector pCAMBIA2300-NAT is obtained by homologous recombination (see FIG. 5).

(2) Transformation

Transforming to DH5a competent state, after kanamycin screening, selecting monoclonal to identify colony by PCR, extracting plasmid from positive colony and confirming that pCAMBIA2300-NAT is correct after sequencing, so genetic transformation may be carried out.

(3) Construction of Overexpression Transgenic Rice

Figure 6:
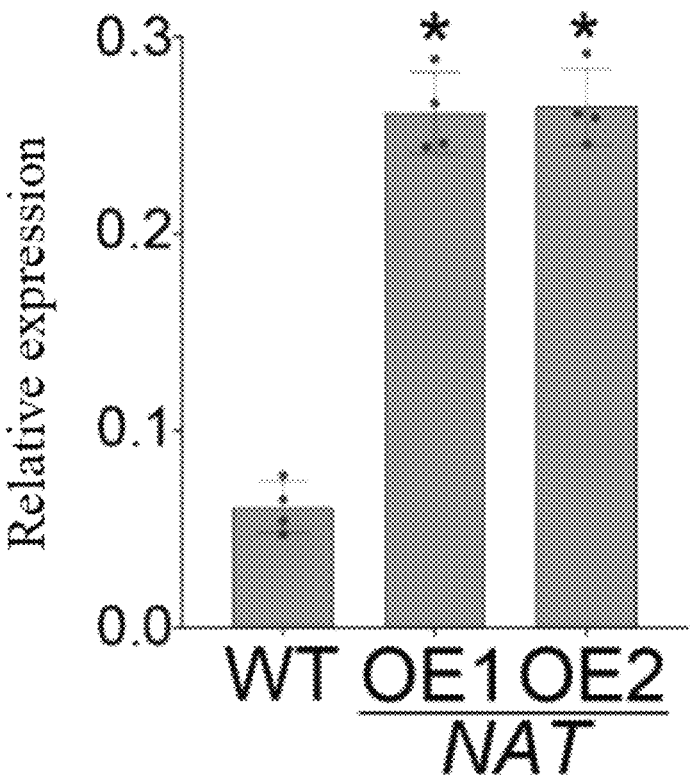
FIG. 6 shows the detection results of NAT expression in wild-type ZH11(WT) and overexpression strains NAT-OE1 and NAT-OE2.

NAT overexpression transgenic rice is completed by Boyuan Biotechnology Company. NAT overexpression strains NAT-EO1 and NAT-EO2 with ZH11 background and genetic stability are selected and sequenced. Compared with the wild-type strain sequence, it is found that the relative expression of NAT in the overexpression strain increases significantly, as shown in FIG. 6.

Embodiment 4 Detection of Disease Resistance of NAT Regulated and Controlled Plants The applicant finds for the first time that NATs protein NAT is involved in regulating the synthesis of jasmonic acid in rice, which is a regulator of jasmonic acid pathway. Jasmonic acid is known as a defense hormone, which plays an important role in regulating and controlling plant disease resistance. Therefore, the effect of NAT on rice disease resistance is tested.

Pricking inoculation treatment at seedling stage: the tested materials are ZH11, NAT knockout strains NAT-KO1 and NAT-KO2 with ZH11 background and genetic stability, and NAT overexpression strains NAT-EO1 and NAT-EO2 with ZH11 background and genetic stability. Selecting seeds with full grain shape, putting them in a conical bottle filled with tap water, putting them in a dark incubator at 37° C. for germination, and changing the water every day. Two days later, the exposed seeds are selected and placed in a 96-hole seedling plate, and the 96-hole seedling plate is placed on a float to grow in Hoagland nutrient solution. Twenty-one days later, the penultimate rice leaf with the same growth and size is selected and inoculated with 5 μL of Zhong Oct. 8, 2014 *M. oryzae* spores with a concentration of $5 \times 10^5 \cdot mL^{-1}$ after pricking. After five days, the length and number of diseased spots are observed and counted.

Spraying treatment at seedling stage: the same as the above-mentioned "pricking inoculation treatment at seedling stage", the penultimate rice leaf with the same growth and size is selected for spraying experiment after 21 days, and the leaf is sprayed with the Zhong Oct. 8, 2014 *M. oryzae* spore solution with the concentration of $5\times10^5 \cdot mL^{-1}$. After 5 days, the length and number of diseased spots are observed and counted.

Figure 7A:
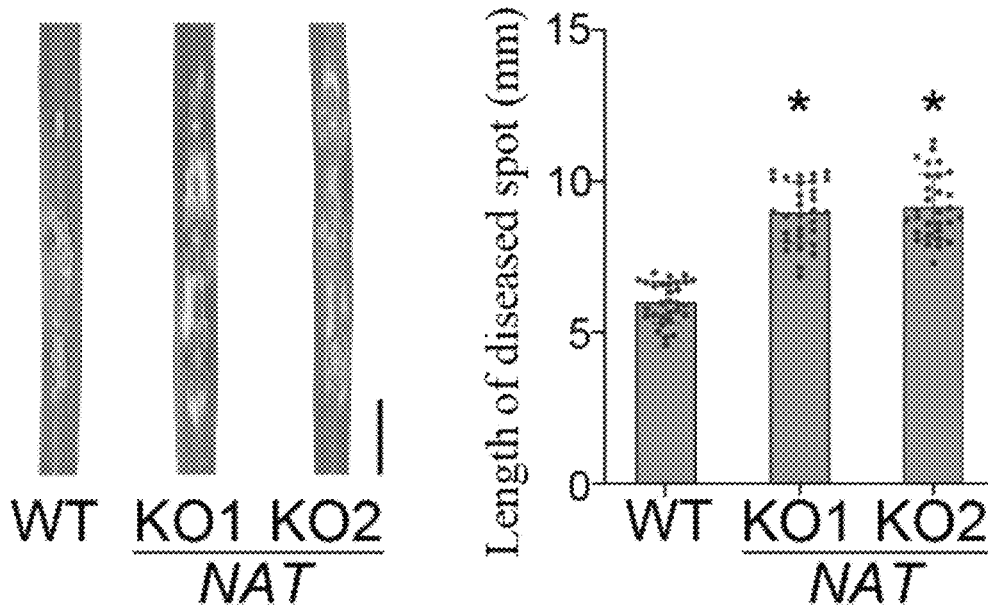
FIG. 7A shows the pricking inoculation results of wild-type ZH11(WT) and knockout strains NAT-KO1 and NAT-KO2 when there is the phenotype of NAT knockout strains inoculated with *M. oryzae*, where the scale is 1 centimeter (cm), and the asterisk above the histogram indicates significant difference (P<0.01).
Figure 7B:
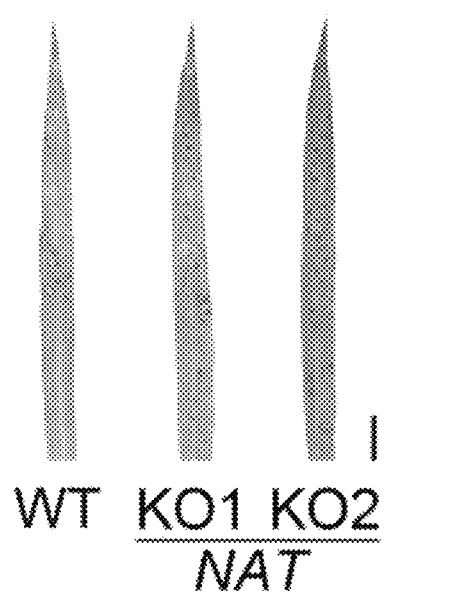
FIG. 7B shows the spray inoculation results of wild-type ZH11(WT) and knockout strains NAT-KO1 and NAT-KO2 when there is the phenotype of NAT knockout strains inoculated with *M. oryzae*, where the scale is 1 cm, and the asterisk above the histogram indicates significant difference (P<0.01).
Figure 7B:
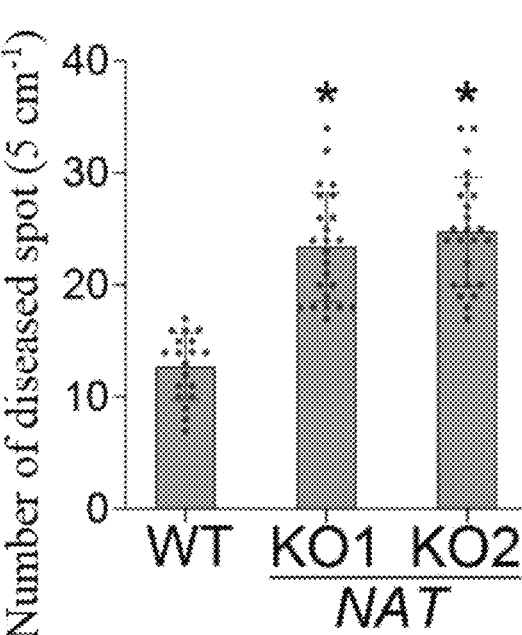
Figure 8A:
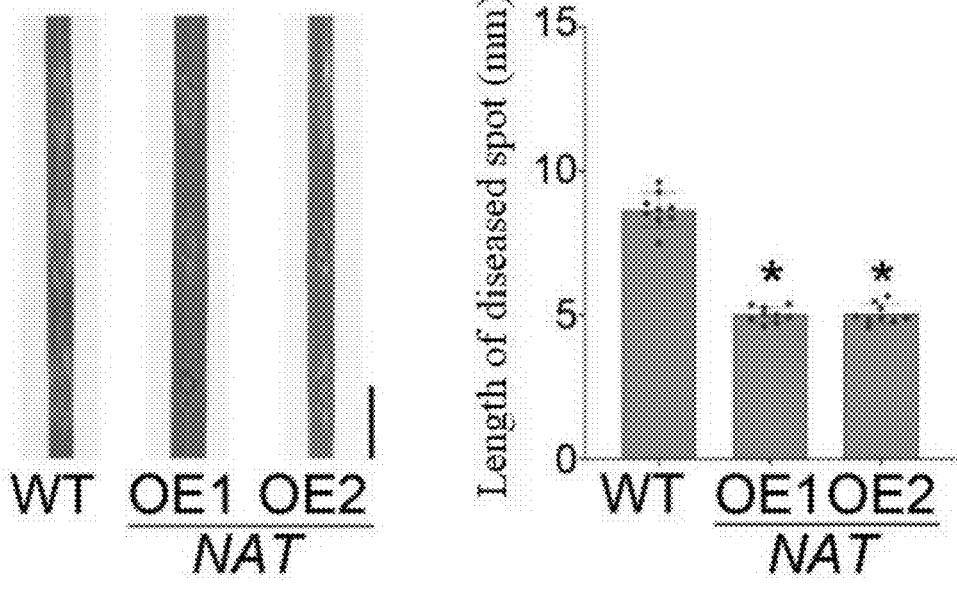
FIG. 8A shows the pricking inoculation results of wild-type ZH11(WT) and overexpression strains NAT-OE1 and NAT-OE2 when there is the phenotype of NAT overexpression strains inoculated with *M. oryzae*, where the scale is 1 cm, and the asterisk above the histogram indicates significant difference (P<0.01).
Figure 8B:
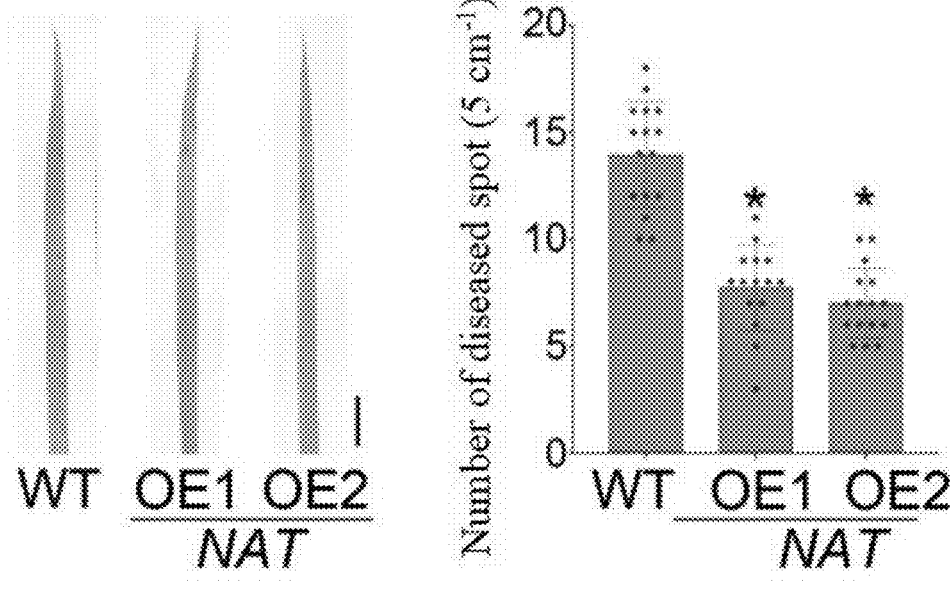
FIG. 8B shows the spray inoculation results of wild-type ZH11(WT) and overexpression strains NAT-OE1 and NAT-OE2 when there is the phenotype of NAT overexpression strains inoculated with *M. oryzae*, where the scale is 1 cm, and the asterisk above the histogram indicates significant difference (P<0.01).

The results shows that there is no significant difference in the growth of ZH11, NAT-KO1, NAT-KO2, NAT-EO1 and NAT-EO2 under hydroponic conditions, and the experimental biology is repeated three times. Each plant has 20 plants at a time. Statistics show that after pricking inoculation, compared with ZH11, the diseased spot length of NAT-KO1 and NAT-KO2 plants under ZH11 background is significantly increased, and they are more sensitive to pathogens (see FIG. 7A and FIG. 7B). However, when NAT is over-expressed in ZH11, the length of the diseased spot is significantly reduced and the disease resistance of the plant is significantly increased (see FIG. 8A and FIG. 8B). It shows that NAT is regulating and controlling plant disease resistance, and its coding gene NAT may be used as a target gene for molecular breeding to improve plant disease resistance.

The above-mentioned embodiments only describe the preferred mode of the disclosure, and do not limit the scope of the disclosure. Under the premise of not departing from the design spirit of the disclosure, various modifications and improvements made by ordinary technicians in the field to the technical scheme of the disclosure shall fall within the protection scope determined by the claims of the disclosure.

What is claimed is:

1. A method for regulating and controlling rice resistance to rice blast, comprising:

improving performance of the rice resistance to the rice blast by overexpressing an N-terminal acetyltransferase (NAT) gene in rice; and wherein the nucleotide sequence of the NAT gene is SEQ ID NO: 1.

2. A method for cultivating transgenic rice with improved resistance to rice blast, comprising following steps: by overexpressing an NAT gene in rice, improving an expression amount of the NAT gene to obtain the transgenic rice with the improved resistance to the rice blast; and wherein the nucleotide sequence of the NAT gene is SEQ ID NO: 1.

* * * * *